US012691106B2

(12) United States Patent
Lam et al.

(10) Patent No.: US 12,691,106 B2
(45) Date of Patent: Jul. 28, 2026

(54) TREATING REFRACTIVE DISORDERS BY TARGETING PEROXISOME PROLIFERATOR-ACTIVATED RECEPTOR (PPAR) SIGNALING PATHWAY

(71) Applicants: Centre for Eye and Vision Research Limited, Hong Kong (HK); The Hong Kong Polytechnic University, Hong Kong (HK)

(72) Inventors: Chuen Lam, Hong Kong (HK); Ying Hon Sze, Hong Kong (HK); Yan Yin Tse, Hong Kong (HK)

(73) Assignees: Centre for Eye and Vision Research Limited, Hong Kong (HK); The Hong Kong Polytechnic University, Hong Kong (HK)

( * ) Notice: Subject to any disclaimer, the term of this patent is extended or adjusted under 35 U.S.C. 154(b) by 487 days.

(21) Appl. No.: 18/332,751

(22) Filed: Jun. 12, 2023

(65) Prior Publication Data

US 2024/0342149 A1      Oct. 17, 2024

Related U.S. Application Data

(60) Provisional application No. 63/496,688, filed on Apr. 17, 2023.

(51) Int. Cl.
*A61K 31/4439*        (2006.01)
*A61P 27/10*        (2006.01)
(52) U.S. Cl.
CPC .......... *A61K 31/4439* (2013.01); *A61P 27/10* (2018.01)
(58) Field of Classification Search
CPC ............................ A61K 31/4439; A61P 27/10
See application file for complete search history.

(56) References Cited

PUBLICATIONS

F.A. Files et al., Local Ocular Compensation for Imposed Local Refractive Error, Vision Research, 1990, 30, 3, 339-349.
Yin Guo et al., Outdoor Jogging and Myopia Progression in School Children From Rural Beijing: The Beijing Children Eye Study, Translational Vision Science & Technology, 2019, 8, 3.
Yun Yun Zhou et al., Proteomic analysis of chick retina during early recovery from lens induced myopia, Molecular Medicine Reports, 2018, 18, 1, 59-66.
Honghui Li et al., Retinal and choroidal expression of BMP-2 in lens induced myopia and recovery from myopia in guinea pigs, Molecular Medicine Reports, 2016, 13, 3, 2671-2676.
Rachel Ka Man Chun et al., Cyclic Adenosine Monophosphate Activates Retinal Apolipoprotein A1 Expression and Inhibits Myopic Eye Growth, Investigative Ophthalmology & Visual Science, 2015, 56, 13, 8151-8157.
Miaozhen Pan et al. PPARγ modulates refractive development and form deprivation myopia in Guinea pigs, Experimental Eye Research, 2021, 202, 108332.
Miaozhen Pan et al. Opposing Effects of PPARa Agonism and Antagonism on Refractive Development and Form Deprivation Myopia in Guinea Pigs, Investigative Ophthalmology & Visual Science, 2018, 59(15), 5803-5815.

*Primary Examiner* — Timothy R Rozof
(74) *Attorney, Agent, or Firm* — Idea Intellectual Limited; Sam T. Yip

(57)        ABSTRACT

A pharmacologic treatment of refractive disorders, specifically myopia or hyperopia, by targeting the PPAR signaling pathway using a PPARγ agonist without any binding to PPARα. It is demonstrated that the PPARγ agonist modulates ocular growth through therapeutic intervention at the protein level of the PPAR signaling pathway. The effectiveness of the PPARγ agonist in regulating the PPAR signaling pathway and its associated proteins, as evidenced by experiments using a lens-induced myopia (LIM) animal model. More particularly, it is also demonstrated that the pharmacological reduction of myopic eye growth in terms of biometrics with dosage effect through the administration of the PPARγ agonist.

7 Claims, 1 Drawing Sheet

TREATING REFRACTIVE DISORDERS BY TARGETING PEROXISOME PROLIFERATOR-ACTIVATED RECEPTOR (PPAR) SIGNALING PATHWAY

CROSS-REFERENCE TO RELATED APPLICATIONS

The present application claims priority from U.S. provisional patent application Ser. No. 63/496,688 filed Apr. 17, 2023, and the disclosure of which is incorporated herein by reference in its entirety.

FIELD OF THE INVENTION

The present invention generally relates to the field of ophthalmology. More specifically the present invention relates to refractive disorders.

BACKGROUND OF THE INVENTION

Myopia is a prevalent ocular disorder, affecting approximately 30% of the global population and projected to increase to 50% by 2050. Individuals with high myopia are at an elevated risk of developing blinding conditions such as myopic maculopathy, retinal detachment, and glaucoma. To slow down the progression of myopia in children and prevent the development of high myopia, various treatments have been developed, which can be classified into two main categories: optical and pharmaceutical. The former includes specialized spectacle lenses and contact lenses, while the latter is primarily represented by atropine eye drops. In mainland China, low-dose atropine eye drops (0.01%-0.05%) are commonly used as the first line of treatment and occupy an estimated 40-50% of the market for myopia management.

While atropine has been demonstrated to be effective in treating myopia, its application is limited by various side effects, such as photophobia, blurry near vision, allergic conjunctivitis, and systemic side effects. Furthermore, the mechanism by which atropine works against myopia is not well understood. Because atropine can be toxic at higher doses, the Chinese Food and Drug Administration (cFDA) has been hesitant to approve its clinical use for the purpose of myopia management. Currently, only the lowest dosage of atropine is permitted for prescription under strict regulations. Furthermore, apart from Atropine, there are various small molecules, biologics, and proteins published in research journals or clinical trials that are reported to be associated with myopia control but none of them has been approved or clinically accepted for routine myopia control in children.

It has been suggested that regulation of eye growth is a homeostasis process depending on the balance of "Growth" and "STOP" signals (Wallman, 1990) optically and biochemically. "Growth" signals accelerate the axial length (AL) elongation, and the "STOP" signal blocks AL elongation. In experimental animal models, myopia can be induced by mounting a negative lens to the eyes, the image will focus behind the retina, (imposing an optical Growth signal (hyperopic defocus), triggering a cascade of biochemical Growth signal, increasing the AL elongation rate. During a recovery treatment after negative lens removal, the eye is exposed to an image focused in front of the retina, imposing an optical STOP signal (myopic defocus), triggering a cascade of biochemical STOP signals (Guo et al., 2019, Zhou et al., 2018b, Li et al., 2016a, Chun et al., 2011). In addition, it is generally accepted that the biochemical signal cascades originate at the retina and end in the sclera. To date, the exact molecular mechanism underlying myopia remains unclear. There is currently no FDA approved or cFDA drug for clinical use.

Proteomic approaches have become powerful tools to screen thousands of protein candidates simultaneously, which enables the detection of global regulation of protein expression. For discovery-based proteomics, the SWATH-MS based proteomics approach has emerged as an increasingly popular platform for biomarker discovery and understanding of biological mechanisms. The literature has demonstrated the potential involvement of the peroxisome proliferator-activated receptor (PPAR) signaling pathway in reducing axial elongation of the eye and slowing myopia progression (PMID: 33152389, 30521668). However, while the involvement of the PPAR signaling pathway has been proposed in literature, supporting molecular biology results have been lacking.

To address this significant gap in clinical treatment, the field is actively seeking an alternative pharmaceutical candidate that offers comparable effectiveness with lower toxicity and fewer side effects. Therefore, the present invention addresses this need.

SUMMARY OF THE INVENTION

The present invention relates to the treatment of refractive disorders using a PPARγ agonist. Specifically, in accordance with one embodiment of the present invention, the present invention encompasses a method of treating refractive disorders, such as myopia or hyperopia, by administering a PPARγ agonist that selectively binds to PPARγ without any binding to PPARα.

In accordance with one embodiment of the present invention, the PPARγ agonist is selected from a thiazolidinedione class.

In accordance with one embodiment of the present invention, the PPARγ agonist may be rosiglitazone or a pharmaceutically acceptable salt thereof.

In accordance with a second aspect of the present invention, a pharmaceutical composition including a PPARγ agonist along with a pharmaceutically acceptable addition for treating a refractive disorder in a subject in need thereof is provided.

In accordance with one embodiment of the present invention, the refractive disorder is selected from myopia or hyperopia.

In accordance with one embodiment of the present invention, the PPARγ agonist selectively binds to PPARγ without any binding to PPARα.

In accordance with one embodiment of the present invention, the PPARγ agonist is selected from a thiazolidinedione class.

In accordance with one embodiment of the present invention, the PPARγ agonist may be rosiglitazone or a pharmaceutically acceptable salt thereof.

In accordance with one embodiment of the present invention, the pharmaceutically acceptable addition includes an excipient, a stability additive, a carrier, a diluent, and a solubilizer.

In accordance with one embodiment of the present invention, the composition may be formulated to an administration form that enables delivery to the patient's retina through the cornea and/or the blood-retinal barrier.

In accordance with one embodiment of the present invention, the administration form is selected from an immediate-release form or a controlled-release form.

In accordance with one embodiment of the present invention, the administration form includes an injection form, an eye drop form, an eye ointment form, a hydrogel form, an ultrasonic ocular drug delivery form, and a drug-loaded contact lenses form.

In accordance with a third aspect of the present invention, a use of a pharmaceutical composition including a PPARγ agonist for treating a refractive disorder in a subject in need thereof is provided.

In accordance with one embodiment of the present invention, the refractive disorder is selected from myopia or hyperopia.

In accordance with one embodiment of the present invention, the PPARγ agonist is selected from a thiazolidinedione class.

In accordance with one embodiment of the present invention, the PPARγ agonist may be rosiglitazone or a pharmaceutically acceptable salt thereof.

Overall, the invention provides an effective approach for treating refractive disorders using a PPARγ agonist, with specific embodiments including the method, pharmaceutical composition, and use as described above.

BRIEF DESCRIPTION OF THE DRAWINGS

Embodiments of the invention are described in more details hereinafter with reference to the drawings, in which.

DETAILED DESCRIPTION

Figure 1:
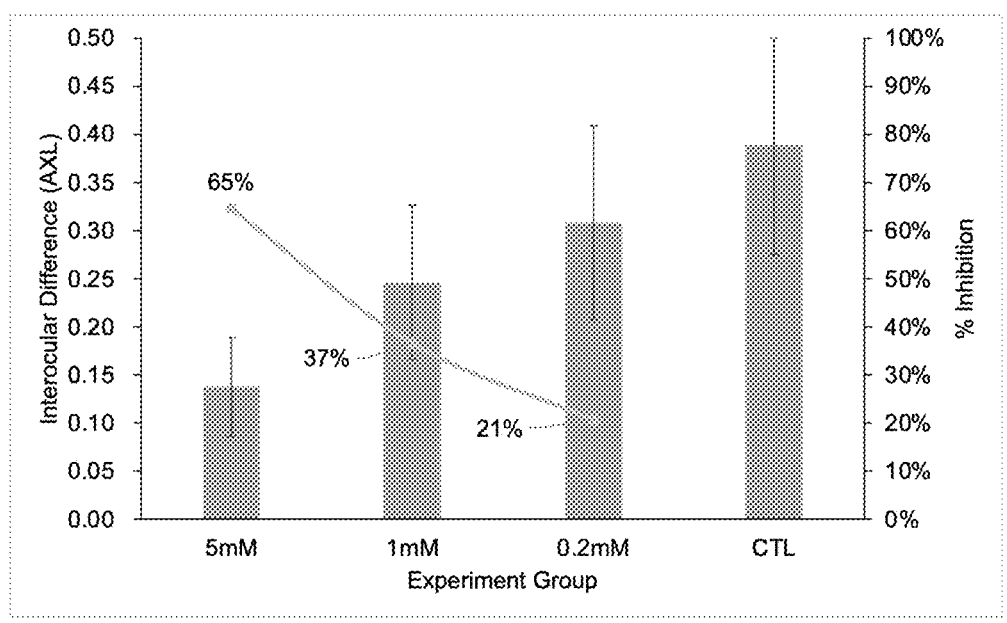
FIG. 1 depicts the effect of myopia control in terms of axial length at different drug dosages.

In the following description, methods and combinations of treating refractive disorders and the likes are set forth as preferred examples. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation.

In accordance with a first aspect of the present invention, a method of treating a refractive disorder is provided. The method includes administering a PPARγ agonist to activate PPAR signaling pathway is provided. More specifically, the pharmacologic treatment of refractive disorders including, myopia and hyperopia, through targeting the PPAR signaling pathway using a pure agonist of PPARγ with no PPARα-binding action is provided.

The term "PPARγ agonist" is an agent which binds to PPARγ to activate or enhance transcriptional activity of a PPARγ receptor. In certain embodiments, an agonist may induce activation of transcription by PPARγ transcriptional complexes by mimicking a natural ligand for the receptor.

A "PPARγ partial agonist" is an agent which binds to PPARγ to activate or enhance the transcriptional activity of a PPARγ receptor. However, a "partial agonist" also has some antagonist activity and can antagonize the agonist activity of a full PPARγ agonist. Partial agonists are characterized by dose-response curves which, even at the upper end, provide less than the full activation of the PPARγ receptor which can be achieved with a full PPARγ agonist such as rosiglitazone.

A "selective" or "specific" PPARγ ligand, modulator, agonist, or partial agonist is one which interacts preferentially with PPARγ as compared to PPARα, PPARβ, and PPARδ (e.g., can activate, bind to, or inhibit the PPARγ receptor at concentration levels which do not appreciably activate, bind to, or inhibit these of other PPAR receptors).

In one embodiment, the PPARγ agonist is selected from a thiazolidinedione class.

The term "thiazolidinedione (TZD)" is a class of a class of heterocyclic compounds consisting of a five-membered $C_3NS$ ring and usually refers to a family of drugs used in the treatment of diabetes mellitus type 2. TZDs act by activating PPARs, specific for PPARγ. The members of this class are derivatives of the parent compound thiazolidinedione, and include but not limited to: rosiglitazone, pioglitazone, lobeglitazone, troglitazone, englitazone, netoglitazone, rivoglitazone, balaglitazone, farglitazar, ciglitazone, darglitazone, LSN862, PAT5A, FK614, MCC-555, MK-0767 and TZD18.

In one embodiment, the PPARγ agonist is an antidiabetic drug, rosiglitazone or a pharmaceutically acceptable salt thereof.

Rosiglitazone, an FDA approved antidiabetic drug, is a known selective PPARγ agonist. Rosiglitazone is an TRPC5 activator and TRPM3 inhibitor. Rosiglitazone is a member of the thiazolidinedione class of agents used to treat type 2 diabetes mellitus. This class of agents improves glycemic control by improving insulin sensitivity. Rosiglitazone can be used in the research of obesity and diabetes, senescence, ovarian cancer to activate PPAR signaling pathway, can dose-dependently suppress axial length growth by 65%. Statistical difference was recorded from 200 μmol to 5 mmol dosages.

"Pharmaceutically acceptable salts" includes derivatives of the compounds, wherein the parent compound is modified by making non-toxic acid or base addition salts thereof, and further refers to pharmaceutically acceptable solvates, including hydrates, of such compounds and such salts. Examples of pharmaceutically acceptable salts include, but are not limited to, mineral or organic acid addition salts of basic residues such as amines; alkali or organic addition salts of acidic residues such as carboxylic acids; and the like, and combinations comprising one or more of the foregoing salts. The pharmaceutically acceptable salts include non-toxic salts and the quaternary ammonium salts of the parent compound formed, for example, from non-toxic inorganic or organic acids. For example, non-toxic acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, and combinations comprising one or more of the foregoing salts. Pharmaceutically acceptable organic salts includes salts prepared from organic acids such as acetic, trifluoroacetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC\text{-}(CH_2)n\text{-}COOH$ where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, asparginate, glutamate, and the like; and combinations comprising one or more of the foregoing salts. A preferred salt of rosiglitazone is the maleate salt, and a preferred salt of metformin is the hydrochloride salt.

In accordance with a second aspect of the present invention, a pharmaceutical composition including a PPARγ agonist along with a pharmaceutically acceptable addition for treating a refractive disorder in a subject in need thereof is provided.

In one embodiment, the refractive disorder is selected from myopia or hyperopia.

In one embodiment, the PPARγ agonist selectively binds to PPARγ without any binding to PPARα.

In one embodiment, the PPARγ ligand may be rosiglitazone or a pharmaceutically acceptable salt thereof.

In one embodiment, the pharmaceutically acceptable addition includes an excipient, a stability additive, a carrier, a diluent, and a solubilizer.

In one embodiment, the composition is formulated to an administration form that enables delivery to the patient's retina through the cornea and/or the blood-retinal barrier.

In one embodiment, the administration form is selected from an immediate-release form or a controlled-release form.

In one embodiment, the administration form includes an injection form, an eye drop form, an eye ointment form, a hydrogel form, an ultrasonic ocular drug delivery form, and a drug-loaded contact lenses form.

Drug formulation and delivery system are crucial for ophthalmic applications. The delivery of the PPARγ agonist is necessary to pass through the cornea and/or the blood-retinal barrier and reach the retina. The delivery technologies encompass the following characteristics: (1) easy and noninvasive administration; (2) an efficient delivery system; (3) compatible with ocular tissues; (4) target-specific for the indicated ocular diseases; and (5) a controlled-release system, which keeps active agents for a prolonged period (several months to several years) in the retina.

Sustained-release formulations of rosiglitazone can be administered once daily or even less frequently. Sustained-release formulations can be based on matrix technology. In this technology, rosiglitazone is embedded in an excipient that makes a non-disintegrating core called a matrix. Diffusion of rosiglitazone occurs through the core.

A pulsed-release dosage form includes an immediate-release dosage form including rosiglitazone or a pharmaceutically acceptable salt thereof; and a delayed-release dosage form including rosiglitazone or a pharmaceutically acceptable salt thereof.

In one embodiment, a delayed-release dosage form can be combined with an immediate-release dosage form to provide a pulsed-release dosage form. The delayed-release dosage form may be in the form of a core which optionally includes absorption enhancers and/or water swellable substances. Pulsed-release dosage forms allow for control of the plasma levels of rosiglitazone.

In one embodiment, the composition is delivered by a nanoparticle or microemulsion drug delivery system, which enhances solubility and improve delivery efficiency by surface-conjugating active targeting agonists or improves drug solubilization capacity and bioavailability. Moreover, the systems also reduce drug toxicity, prolong the residence time, and protect biological drugs from degradation. Another direction is the integration of nanotechnology with other delivery systems, such as ultrasonic ocular drug delivery systems, drug-loaded contact lenses, and hydrogel.

The term of "immediate-release" means that a conventional or non-modified release form in which greater than or equal to about 75% of the active agent is released within two hours of administration, preferably within one hour of administration.

The term "controlled-release" is a dosage form in which the release of the active agent is controlled or modified over a period of time. Controlled can mean, for example, sustained, delayed or pulsed-release at a particular time. Alternatively, controlled can mean that the release of the active agent is extended for longer than it would be in an immediate-release dosage form, i.e., at least over several hours, such as greater than four hours, preferably greater than eight hours.

The term "sustained-release" or "extended-release" is meant to include the release of the active agent at such a rate that blood (e.g., plasma) levels are maintained within a therapeutic range but below toxic levels for at least about 8 hours, preferably at least about 12 hours after administration at steady-state. The term "steady-state" means that a plasma level for a given active agent has been achieved and which is maintained with subsequent doses of the drug at a level which is at or above the minimum effective therapeutic level and is below the minimum toxic plasma level for a given active agent.

The term "delayed-release" means that there is a time-delay before significant plasma levels of the active agent are achieved. A delayed-release formulation of the active agent can avoid an initial burst of the active agent, or can be formulated so that release of the active agent in eye ball or muscle layer is avoided and absorption takes places in retina.

A "pulsed-release" formulation can contain a combination of immediate-release, sustained-release, and/or delayed-release formulations in the same dosage form. A "semi-delayed-release" formulation is a pulsed-released formulation in which a moderate dosage is provided immediately after administration and a further dosage some hours after administration.

In accordance with a third aspect of the present invention, a use of a pharmaceutical composition including a PPARγ agonist for treating a refractive disorder in a subject in need thereof is provided.

In one embodiment, the refractive disorder is selected from myopia or hyperopia.

In one embodiment, the PPARγ agonist may be rosiglitazone or a pharmaceutically acceptable salt thereof.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including", and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in a suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

EXAMPLES

Using animal experimentation and bioinformatics, a potential off-label use of a diabetic drug targeting the PPAR signaling pathway at the protein level is identified, demonstrating altered ocular growth through therapeutic intervention. The present invention is the first to demonstrate the involvement of this off-label use of the drug in targeting the PPAR signaling pathway and associated proteins, using a lens-induced myopia (LIM) animal model. Most significantly, the pharmacological reduction of myopic eye growth in terms of biometrics with dosage effect through the off-label use of this diabetic drug is demonstrated.

Example 1. Effect of Rosiglitazone on Reducing Axial Elongation in Lens-Induced Myopia Chicks age day 7 are divided into 2 groups, lens-induced myopia (LIM) and age-matched control (CTL), randomly. Chick eyes are measured with ultrasonic A-scan and refractive index by retinoscope by a single-masked operator. A computer-controlled randomization is applied to assign either left or right eye for LIM treatment and contralateral eye served as untouch control. Baseline physiological data is acquired on day 7. Purified rosiglitazone (>99%) is purchased from manufacturer and dissolved in 100% Dimethyl sulfoxide (DMSO). A working rosiglitazone solution is prepared in the concentration of 5 mM in 2% DMSO, PBS solution prior use. The rosiglitazone (5 mM, 10 μL) is delivered by intravitreal injection in the LIM eye once a day for 3 consecutive days. A-10 D lens is applied soon after drug delivery. Chick eyes are measured again on day 10 to access the effect of rosiglitazone.

Further, the effect of rosiglitazone in lower dosages is also investigated. Briefly, chicks age day 7 are divided into 3 groups, lens-induced myopia with higher dosage (LIM with 1 mM, n=7), lens-induced myopia with lower dosage (LIM with 0.2 mM, n=7) and age-matched control (CTL, n=2), randomly. Chick eyes are measured with ultrasonic A-scan and refractive index by retinoscope by a single-masked operator. A computer-controlled randomization is applied to assign either left or right eye for LIM treatment and contralateral eye served as untouched control. Baseline physiological data is acquired on day 7. Purified rosiglitazone (>99%) is purchased from manufacturer and dissolved in 100% Dimethyl sulfoxide (DMSO). A working rosiglitazone solution is prepared in the concentration of 5 mM in 2% DMSO, PBS solution prior use. The rosiglitazone (1 mM, 10 μL or 0.2 mM, 10 μL) is delivered by intravitreal injection in the LIM eye once a day for 3 consecutive days. A-10 D lens is applied soon after drug delivery. Chick eyes are measured again on day 10 to access the effect of rosiglitazone.

Referring to FIG. 1, the rosiglitazone treatment has shown a consistent effect on slowing myopia progression by an average of 65% using different batches of chicks when compared to independent age-matched chicks subjected to LIM treatment. The effect of myopia inhibition is reduced with dose with an exponential regression of $y=1.14e^{-0.57x}$, $R^2=1$) to 37% of inhibition in 1 mM drug and 21% of inhibition in 0.2 mM drug treatment group.

Example 2. Effects of Rosiglitazone on Normal Eyes

Chicks age day 7 (n=5) are measured with ultrasonic A-scan and refractive index by retinoscope by a single-masked operator. A computer-controlled randomization is applied to assign either left or right eye for drug treatment and contralateral eye served as untouched control. Baseline physiological data is acquired on day 7. Purified rosiglitazone (>99%) is purchased from manufacturer and dissolved in 100% Dimethyl sulfoxide (DMSO). A working rosiglitazone solution is prepared in the concentration of 5 mM in 2% DMSO, PBS solution piror use. The rosiglitazone (5 mM, 10 μL) is delivered by intravitreal injection in the LIM eye once a day for 3 consecutive days. A-10 D lens is applied soon after drug delivery. Chick eyes are measured again on day 10 to access the effect of the rosiglitazone.

Figure 2:
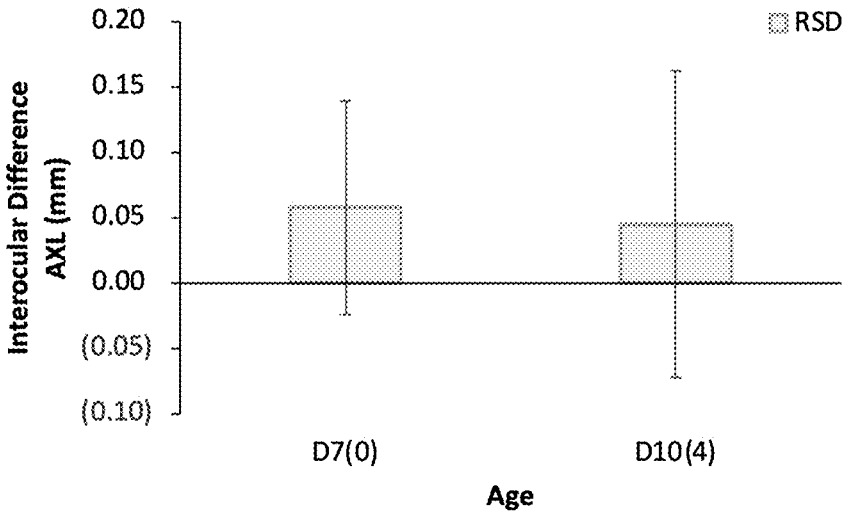
FIG. 2 depicts the effect of 5 mM rosiglitazone on normal eyes at two time points.

As shown in FIG. 2, rosiglitazone has no statistically significant effect on normal growing eye or inducing hyperopia in naked eye (visual manipulation treatments).

In summary, the rosiglitazone shows high effectiveness and no sign of toxicity so far in our animal models. The exact mechanism underlying the existing drug "atropine" is unclear. In contrast, the PPAR signaling pathway is screened in mice neural retina and rosiglitazone is evaluated in chick model showing the effect of slowing myopic progression, by SWATH-MS acquisition and ultrasonic scan to monitor axial elongation in eye. The SWATH-MS-based proteomics approach has emerged as an increasingly popular platform for biomarker discovery and understanding of biological mechanisms, with advantages of high reproducibility, high resolution, and high speed of protein detection. Therefore, the invention is raised based on more accurate and reliable techniques with molecular biology rationale.

The effect of rosiglitazone on myopic mammalian models are evaluated. Further, gene editing or knockdown of targets in the PPAR signaling pathway in mice is conducted and various drugs targeting other nodes on the PPAR signaling pathway are also screened.

As used herein, terms "approximately", "basically", "substantially", and "about" are used for describing and explaining a small variation. When being used in combination with an event or circumstance, the term may refer to a case in which the event or circumstance occurs precisely, and a case in which the event or circumstance occurs approximately. As used herein with respect to a given value or range, the term "about" generally means in the range of ±10%, ±5%, ±1%, or ±0.5% of the given value or range. The range may be indicated herein as from one endpoint to another endpoint or between two endpoints. Unless otherwise specified, all the ranges disclosed in the present disclosure include endpoints. The term "substantially coplanar" may refer to two surfaces within a few micrometers (μm) positioned along the same plane, for example, within 10 μm, within 5 μm, within 1 μm, or within 0.5 μm located along the same plane. When reference is made to "substantially" the same numerical value or characteristic, the term may refer to a value within ±10%, ±5%, ±1%, or ±0.5% of the average of the values.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated.

The invention claimed is:

1. A method of treating a refractive disorder, comprising administering a PPARγ agonist, wherein the PPARγ agonist selectively binds to PPARγ without any binding to PPARα, and wherein the PPARγ agonist is rosiglitazone or a pharmaceutically acceptable salt thereof.

2. The method of claim 1, wherein the refractive disorder is selected from myopia or hyperopia.

3. The method of claim 1, further comprising administering a pharmaceutically acceptable addition.

4. The method of claim 3, wherein the pharmaceutically acceptable addition comprises an excipient, a stability additive, a carrier, a diluent, or a solubilizer.

5. The method of claim 1, wherein the administration of the PPARγ agonist being an administration form of that enables delivery to the patient's retina through the cornea and/or the blood-retinal barrier.

6. The method of claim 5, wherein the administration form is selected from an immediate-release form or a controlled-release form.

7. The method of claim 6, wherein the administration form comprises an injection form, an eye drop form, an eye ointment form, a hydrogel form, an ultrasonic ocular drug delivery form, and a drug-loaded contact lenses form.

\* \* \* \* \*